United States Patent [19]

Itoh et al.

[11] Patent Number: 5,473,037
[45] Date of Patent: Dec. 5, 1995

[54] METHOD OF PRODUCING DIMETHYLPOLYSILOXANES

[75] Inventors: Kunio Itoh; Toshio Shinohara, both of Takasaki; Hiroaki Kizaki, Annaka; Shoichi Tanaka, Annaka; Yukinori Satou, Annaka; Kazunobu Umemura, Annaka, all of Japan

[73] Assignee: Shin-Etsu Chemical Co. Ltd., Tokyo, Japan

[21] Appl. No.: 291,067

[22] Filed: Aug. 17, 1994

[30] Foreign Application Priority Data

Aug. 18, 1993 [JP] Japan .................... 5-226439

[51] Int. Cl.$^6$ .................................. C08G 77/08
[52] U.S. Cl. ........................... 528/12; 528/10; 528/23; 556/450; 556/452; 556/460
[58] Field of Search ................... 556/450, 452, 556/460; 528/12, 10, 23

[56] References Cited

U.S. PATENT DOCUMENTS

| | | | |
|---|---|---|---|
| 2,381,366 | 8/1945 | Patnode | 556/452 |
| 2,470,479 | 5/1949 | Ferguson et al. | |
| 2,645,628 | 7/1953 | Hurd | 556/460 |
| 3,489,782 | 1/1970 | Pruvost | 528/10 |
| 3,627,805 | 12/1971 | Thomas et al. | 556/460 |
| 3,786,015 | 1/1974 | Merrill et al. | 528/10 |
| 3,790,527 | 2/1974 | Merrill | 528/23 |
| 3,846,358 | 11/1974 | Roedel | |
| 5,075,479 | 12/1991 | Borerman et al. | 556/452 |

FOREIGN PATENT DOCUMENTS

| | | |
|---|---|---|
| 938256 | 7/1946 | France . |
| 2345923 | 3/1980 | Germany . |
| 631018 | 10/1942 | United Kingdom . |

*Primary Examiner*—Melvyn I. Marquis
*Attorney, Agent, or Firm*—Millen, White, Zelano & Branigan

[57] ABSTRACT

Disclosed is a method of producing dimethylpolysiloxanes through hydrolysis of dimethyldichlorosilane wherein a water solution containing a water-soluble oxygen-containing organic compound is introduced into dimethyldichlorosilane. Therein, linear dimethylpolysiloxanes alone having both ends blocked with chlorine atoms can be selectively produced by properly controlling the water content in the hydrolysis system and further by rendering the hydrolysis system acidic, and cyclic dimethylpolysiloxanes alone can also be selectively produced by properly controlling the water content in the hydrolysis system and optionally rendering the hydrolysis system acidic.

15 Claims, 1 Drawing Sheet

METHOD OF PRODUCING DIMETHYLPOLYSILOXANES

FIELD OF THE INVENTION

The present invention relates to a method of producing dimethylpolysiloxanes and, more particularly, to a method of selectively producing either linear dimethylpolysiloxanes alone both ends of which are blocked with chlorine atoms or cyclic dimethylpolysiloxanes alone.

BACKGROUND OF THE INVENTION

A synthesis method for linear methylchloropolysiloxanes has already been reported by Winton Patnode and Donald F. Wilcock in *J. Am. Chem. Soc.*, volume 68, page 358 (1946).

In the above-cited method, a mixture of purified water and dioxane is introduced into dimethyldichlorosilane dissolved in a large quantity of diethyl ether. However, using a large quantity of diethyl ether is dangerous in handling and impairs the production efficiency per unit volume. Therefore, that method has a defect of having no suitability for production on an industrial scale.

In addition, the foregoing report describes experimental results such that a mixture of linear methylchloropolysiloxanes with cyclic dimethylpolysiloxanes is produced when purified water by itself is introduced into dimethyldichlorosilane alone, the linear product and the cyclic product thus obtained are hard to separate because their boiling points are very close to each other, and the linear methylchloropolysiloxanes, which are more useful than the cyclic product, are produced therein in low yields.

In order to solve the above-described problems, therefore, we have made intensive studies. As a result, it has been found out that in hydrolyzing dimethyldichlorosilane by introducing thereinto a water solution containing a water-soluble oxygen-containing organic compound, linear dimethylpolysiloxanes alone, having both ends blocked with chlorine atoms, can be selectively produced when the water solution introduced is rendered acidic and the quantity of water introduced into the hydrolysis system is controlled properly; while cyclic dimethylpolysiloxanes alone can be selectively produced by properly controlling the quantity of water introduced into the hydrolysis system and, if desired, the water solution is rendered acidic; thereby achieving the present invention.

SUMMARY OF THE INVENTION

An object of the present invention is therefore to provide a dimethylpolysiloxane-producing method which enables selective production of linear dimethylpolysiloxanes alone, having both ends blocked with chlorine atoms, or cyclic dimethylpolysiloxanes alone.

The above-described object of the present invention is attained with by a method of producing dimethylpolysiloxanes which comprises carrying out hydrolysis by introducing into dimethyldichlorosilane a water solution containing a water-soluble oxygen-containing organic compound.

Figure 1:
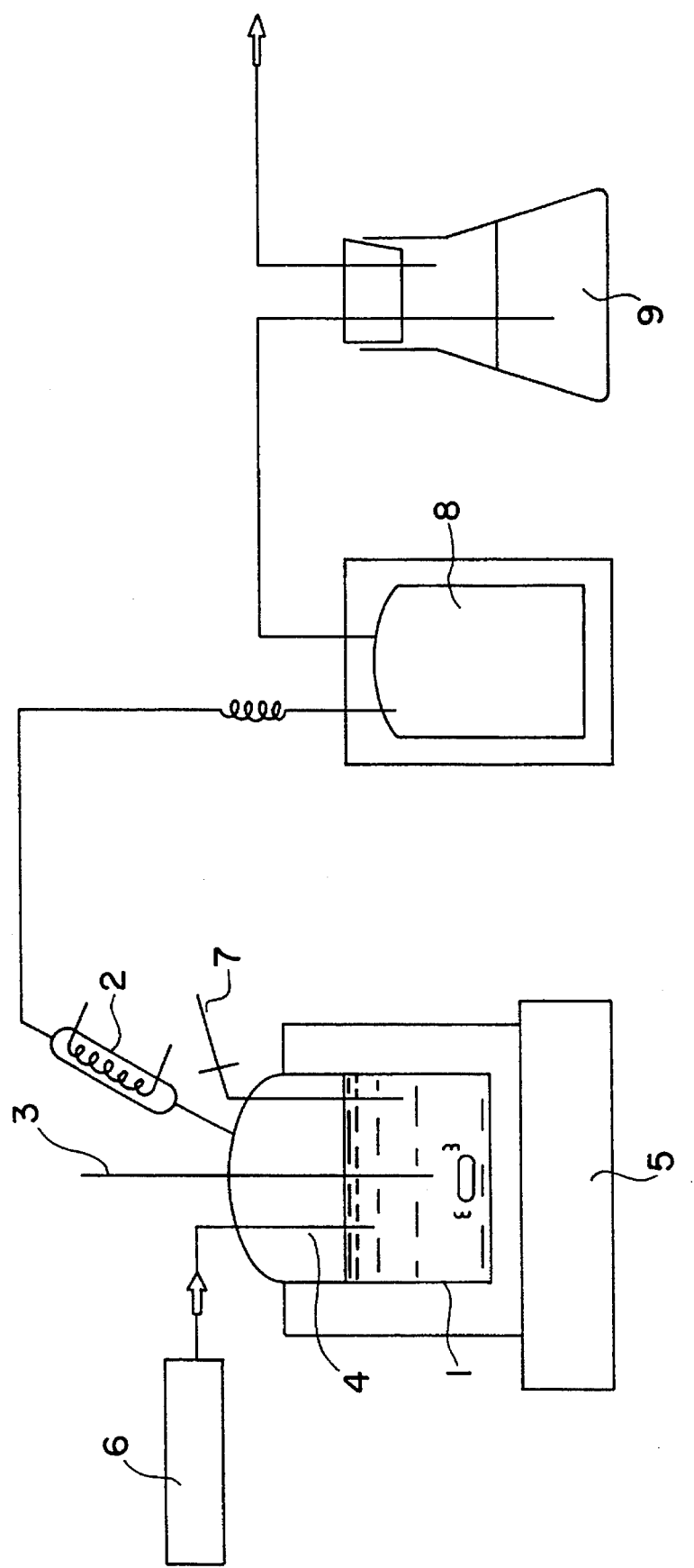
FIG. 1 shows an apparatus used for the synthesis reactions according to the present invention.

Therein, the numeral 1 represents a reaction flask, the numeral 2 a condenser, the numeral 3 a thermometer, the numeral 4 a tube for introduction of water, the numeral 5 a magnetic stirrer, the numeral 6 a microfeeder, the numeral 7 a sampling capillary, the numeral 8 a trap, and the numeral 9 a hydrogen chloride absorber.

DETAILED DESCRIPTION OF THE INVENTION

Suitable examples of a water-soluble oxygen-containing organic compound include alcohols such as methanol, ethanol, etc., ketones such as acetone, methyl ethyl ketone, etc., and cyclic ethers such as 1,3-dioxane, 1,4-dioxane, tetrahydrofuran, etc. Of these compounds, acetone, 1,4-dioxane and tetrahydrofun are particularly preferred over the others since they do not react with dimethyldichlorosilane as a starting material.

These compounds may be used alone or as a mixture of two or more thereof. When they are used as a mixture, however, it becomes difficult to separate the solvent from the reaction product. Accordingly, it is desirable for them to be used independently.

In order to render the water solution acidic, ordinary acids such as hydrochloric acid, sulfuric acid, acetic acid and so on can be used properly. From the industrial point of view, however, hydrochloric acid is especially preferred because of its readiness in recovery.

For the acidic water solution, it is desirable that the ratio of an acid to water (the acid/water ratio by weight) be in the range of 0.001 to 0.35, particularly 0.005 to 0.25. When the acid/water ratio is increased beyond 0.35, the solution is difficult to handle, e.g., in the case of using hydrochloric acid as the acid. This is because the hydrochloric acid in the water solution is gasified at ordinary temperature under ordinary pressure. When the ratio is decreased below 0.001, on the other hand, the water solution has no appreciable effect on the hydrolysis.

As for the amount of the water-soluble oxygen-containing organic compound used, it is desirable that the ratio of the compound to water (the ratio of the weight of the water-soluble oxygen-containing organic compound to the weight of water in the water solution) be in the range of 0.1 to 10, particularly 0.5 to 2.0. This is because an economical advantage is not produced when the compound is used in a ratio greater than 10, while the organic compound cannot achieve its solvent effect when it is used in a ratio smaller than 0.1.

In carrying out the hydrolysis, it is desirable that the foregoing water solution be introduced into dimethyldichlorosilane at a rate of 0.1 to 0.8 g/min per 100 g of dimethyldichlorosilane. When the introduction rate is too high, heat evolution becomes intense, and so it becomes difficult to control the temperature inside the reaction tank. When the introduction rate is too low, on the other hand, it is undesirable from an economical point of view because of its low production efficiency.

When the amount of water added to dimethyldichlorosilane is strictly controlled in the present method, it becomes possible to selectively produce only linear dimethylpelysiloxanes the both ends of which are blocked with chlorine atoms, which are represented by the following general formula (I), and also to selectively produce only cyclic dimethylpolysiloxanes represented by the following general formula (II):

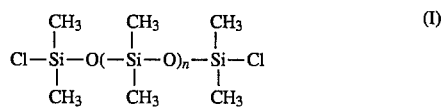

(I)

wherein n is a natural number including 0, preferably from 0 to 12, and particularly preferably from 0 to 2;

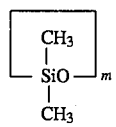

(II)

wherein m is an integer of at least 3, preferably from 3 to 14, and particularly preferably from 4 to 6.

In order to produce only linear dimethylpolysiloxanes having both ends blocked with chlorine atoms, or in other words, in order not to produce cyclic dimethylpolysiloxanes at all, it is required to add water in a proportion of at most 0.5 mole per mole of dimethyldichlorosilane and further to render the water solution acidic.

When the proportion of water is increased beyond the value specified above, the produced dimethylpolysiloxanes having both ends blocked with chlorine atoms are rapidly converted into cyclic siloxanes.

In addition, the value n in general formula (I) can be controlled by keeping the reaction system homogeneous and properly choosing the amount of water added and the reaction temperature.

In order to produce cyclic dimethylpolysiloxanes alone, on the other hand, it is required to add water in a proportion of from 1.0 to 1.2 mole per mole of dimethyldichlorosilane. When the proportion is increased beyond 1.2, there are produced undesirable high-molecular methylpolysiloxanes containing hydroxyl groups as end groups.

In addition, the value m in general formula (II) can be controlled by properly choosing the amount of water added and the reaction temperature.

Preferably, the reaction temperature ranges from 1° C. to 101° C., particularly from 3° C. to 30° C. This is because it sometimes happens that the reaction temperature lower than 1° C. causes the freezing of the water solution introduced, while the reaction temperature higher than 101° C. causes the vaporization of the water solution introduced.

Further hydrolysis makes it possible to eliminate chlorine atoms from the linear dimethylpolysiloxanes represented by general formula (I), and thereby to produce dimethylpolysiloxanes having higher polymerization degrees. Furthermore, the hydrolysis product undergoes the an equilibration reaction with hexamethyldisiloxane in the presence of an acidic catalyst such as sulfuric acid, thereby being converted into the polysiloxanes containing the group $(CH_3)_3SiO-$ as the end groups.

The thus obtained polysiloxanes are inert chemically, and so they can be used as heat-resisting silicone oil.

On the other hand, when the chlorine-eliminated polysiloxanes undergo polymerization in the presence of a basic catalyst such as sodium hydroxide, the polysiloxanes obtained come to have very high molecular weights. Further, when the thus obtained polysiloxanes undergo a crosslinking reaction by heating in the presence of a peroxide, such as benzoyl peroxide, as a catalyst, they are converted into polymers having structural stability. The thus produced polysiloxanes can serve as silicone rubber having excellent heat resistance and weather resistance.

In accordance with the present method of producing dimethylpolysiloxanes, either the linear dimethylpolysiloxanes alone having both ends blocked with chlorine atoms or cyclic dimethylpolysiloxanes alone can be selectively produced. Therefore, the present method has advantages in that (1) it has a capability of realizing a process in which dimethylcyclics are produced without requiring any cracking step, (2) it does not require the separation of waste acid, and so it can have a high pot yield, (3) it enables a considerably great reduction of cost in production on an industrial scale, (4) it can provide linear oligomers serving as intermediates applicable for various purposes, and so on.

Now, the present invention is illustrated below in greater detail by reference to the following examples and comparative examples. However, the invention should not be construed as being limited to these examples.

EXAMPLES

All the synthesis reactions were carried out using a reaction apparatus shown in FIG. 1.

The flask 1 used therein had a volume of 500 ml and was equipped with a condenser 2, a thermometer 3, a water introduction tube 4 and a magnetic stirrer 5. Dimethyldichlorosilane was placed in the flask, and a water solution containing a water-soluble oxygen-containing organic compound and, if needed, an acid (preferably hydrochloric acid) was introduced into the flask from a microfeeder 6 as the reaction temperature was controlled with a means placed outside the flask.

The quantity of an intended methylchloropolysiloxane produced was examined by collecting a small volume of reaction mixture through a sampling tube 7 and analyzing it by gas chromatography.

When hydrogen chloride gas was evolved as a by-product, it was passed through the condenser 2, cooled with methanol-dry ice, passed through a trap 8, and then trapped with an absorber 9 in which water was charged.

Example 1

A water solution to be introduced was prepared by mixing 49 g of dioxane, 1 g of hydrogen chloride and 50 g of water. This solution was injected at a speed of 0.5 g/min into 185 g of the dimethyldichlorosilane placed in the flask. The reaction temperature was kept within the range of 6° to 10° C. by the external control.

Synthesis reactions were carried out under the same condition as described above, except that the content of water in the water solution introduced was changed variously. More specifically, the ratios of the water to the dimethyldichlorosilane in these reactions were 0.257, 0.500, 0.600, 0.820, 1.200 and 1.500, respectively, by mole. A small volume of the reaction product in each reaction was collected, and analyzed by gas chromatography. The thus determined yields of the reaction products and the water/dimethyldichlorosilane ratios (by mole) corresponding thereto are summarized in Table 1.

TABLE 1

| H₂O/(CH₂)₂SiCl₂ Ratio (by mole) | Yield (%) of Reaction Product | | | | | | | Note |
|---|---|---|---|---|---|---|---|---|
| | Linear Siloxane | | | Cyclic Siloxane | | | | |
| | 2,2-Dimer | 2,2-Trimer | 2,2-Tetramer | $D_3$ | $D_4$ | $D_5$ | $D_6$ | |
| 0.257 | 75 | 20 | 5 | 0 | 0 | 0 | 0 | Invention |
| 0.500 | 51 | 29 | 20 | 0 | 0 | 0 | 0 | Invention |
| 0.600 | 30 | 20 | 33 | 0 | 10 | 7 | 0 | Comparison |
| 0.820 | 12 | 18 | 40 | 0 | 15 | 15 | 0 | Comparison |
| 1.000 | 0 | 0 | 0 | 0 | 65 | 30 | 5 | Invention |
| 1.200 | 0 | 0 | 0 | 0 | 65 | 29 | 6 | Invention |
| 1.500* | 0 | 0 | 0 | 0 | 45 | 25 | 10 | Comparison |

*When the H₂O/(CH₃)₂SiCl₂ ratio was 1.500, high-molecular methylpolysiloxanes containing hydroxyl groups as end groups were produced in a 20% yield.

As can be seen from Table 1, linear siloxanes alone were produced when the $H_2O/(CH_3)_2SiCl_2$ ratio was 0.500 or lower, while they were not produced at all when the $H_2O/(CH_3)_2SiCl_2$ ratio was 1.000 or higher.

Additionally, the reaction products designated by 2,2-dimer, 2,2-trimer, 2,2-tetramer, $D_3$, $D_4$, $D_5$ and $D_6$ are the compounds represented by the following structural formulae (i), (ii), (iii), (iv), (v), (vi) and (vii), respectively.

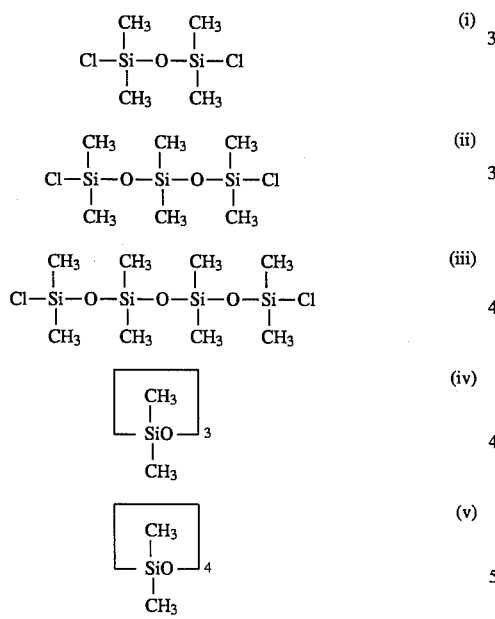

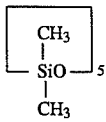

(vi)

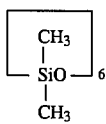

(vii)

Example 2

Synthesis reactions were carried out in the same manner as in Example 1, except that hydrogen chloride was not used at all. The reaction products obtained under the water/dimethyldichlorosilane ratios of 0.257, 0.500, 0.820 and 1.000 respectively were each sampled, and analyzed by gas chromatography. The thus determined yields of the reaction products and the water/dimethyldichlorosilane ratios (by mole) corresponding thereto are summarized in Table 2.

TABLE 2

| H₂O/(CH₃)₂SiCl₂ Ratio (by mole) | Yield (%) of Reaction Product | | | | | | | Note |
|---|---|---|---|---|---|---|---|---|
| | Linear Siloxane | | | Cyclic Siloxane | | | | |
| | 2,2-Dimer | 2,2-Trimer | 2,2-Tetramer | $D_3$ | $D_4$ | $D_5$ | $D_6$ | |
| 0.257 | 72 | 19 | 4 | 0 | 3 | 1 | 1 | Comparison |
| 0.500 | 47 | 28 | 15 | 0 | 7 | 2 | 1 | Comparison |
| 0.820 | 10 | 17 | 34 | 0 | 20 | 19 | 1 | Comparison |
| 1.000 | 0 | 0 | 0 | 0 | 65 | 32 | 3 | Invention |

The data shown in Table 2 indicate that when the water solution introduced was not acidic the cyclic siloxanes ($D_4$, $D_5$, $D_6$), though the yields thereof were low, were produced even when the $H_2O/(CH_3)_2SiCl_2$ ratio was not higher than 0.500 by mole. On the other hand, cyclic siloxanes alone were produced at the $H_2O/(CH_3)_2SiCl_2$ ratio of 1.000 even when the water solution introduced was not acidic.

Comparative Example 1

Synthesis reactions were carried out in the same manner as in Example 1, except that dioxane was not used at all. The reaction products obtained under the water/dimethyldichlorosilane ratios of 0.257, 0.500, 0.820 and 1.000 respectively were each sampled, and analyzed by gas chromatography. The thus determined yields of the reaction products and the water/dimethyldichlorosilane ratios (by mole) corresponding thereto are summarized in Table 3.

TABLE 3

| $H_2O/(CH_3)_2SiCl_2$ Ratio (by mole) | Yield (%) of Reaction Product | | | | | | |
|---|---|---|---|---|---|---|---|
| | Linear Siloxane | | | Cyclic Siloxane | | | |
| | 2,2-Dimer | 2,2-Trimer | 2,2-Tetramer | $D_3$ | $D_4$ | $D_5$ | $D_6$ |
| 0.257 | 32 | 12 | 2 | 0 | 41 | 10 | 3 |
| 0.500 | 24 | 10 | 2 | 0 | 49 | 11 | 4 |
| 0.820 | 17 | 16 | 3 | 0 | 48 | 12 | 4 |
| 1.000 | 16 | 18 | 2 | 0 | 46 | 12 | 6 |

The data shown in Table 3 indicate that the cyclic siloxanes ($D_4$, $D_5$, $D_6$) were produced to a considerable extent even when the ratio of the water in the introduced water solution to the dimethyldichlorosilane was low in value by mole.

Comparative Example 2

Synthesis reactions were carried out in the same manner as in Example 1, except that neither dioxane nor hydrogen chloride was used at all. The reaction products obtained under the water/dimethyldichlorosilane ratios of 0.257, 0.500, 0.820 and 1.000 respectively were each sampled, and analyzed by gas chromatography. The thus determined yields of the reaction products and the water/dimethyldichlorosilane ratios (by mole) corresponding thereto are summarized in Table 4.

TABLE 4

| $H_2O/(CH_3)_2SiCl_2$ Ratio (by mole) | Yield (%) of Reaction Product | | | | | | |
|---|---|---|---|---|---|---|---|
| | Linear Siloxane | | | Cyclic Siloxane | | | |
| | 2,2-Dimer | 2,2-Trimer | 2,2-Tetramer | $D_3$ | $D_4$ | $D_5$ | $D_6$ |
| 0.257 | 22 | 2 | 0 | 0 | 50 | 20 | 6 |
| 0.500 | 13 | 6 | 0 | 0 | 58 | 19 | 4 |
| 0.820 | 10 | 9 | 1 | 0 | 57 | 18 | 5 |
| 1.000 | 8 | 11 | 2 | 0 | 57 | 14 | 8 |

The data shown in Table 4 indicate that the cyclic siloxanes ($D_4$, $D_5$, $D_6$) were produced in higher yields than the linear siloxanes even when the ratio of the water in the introduced water solution to the dimethyldichlorosilane was low in value by mole.

Example 3

Synthesis reactions were performed in the same manner as in Example 1, except that the introduction speed of the water solution was changed to 0.4 g/min and the reaction temperature was kept within the range of 10° to 15° C. In analogy with Example 1, the reaction products obtained under the water/dimethyldichlorosilane ratios of 0.257, 0.500, 0.820 and 1.000 respectively were each sampled, and analyzed by gas chromatography. The thus determined yields of the reaction products and the water/dimethyldichlorosilane ratios (by mole) corresponding thereto are summarized in Table 5.

TABLE 5

| $H_2O/(CH_2)_2SiCl_2$ Ratio (by mole) | Yield (%) of Reaction Product | | | | | | | |
|---|---|---|---|---|---|---|---|---|
| | Linear Siloxane | | | Cyclic Siloxane | | | | |
| | 2,2-Dimer | 2,2-Trimer | 2,2-Tetramer | $D_3$ | $D_4$ | $D_5$ | $D_6$ | Note |
| 0.257 | 70 | 20 | 10 | 0 | 0 | 0 | 0 | Invention |
| 0.500 | 48 | 28 | 24 | 0 | 0 | 0 | 0 | Invention |
| 0.820 | 11 | 15 | 35 | 0 | 20 | 19 | 0 | Comparison |
| 1.000 | 0 | 0 | 0 | 0 | 65 | 30 | 5 | Invention |

Example 4

A water solution to be introduced was prepared by mixing 49 g of acetone, 5 g of hydrogen chloride and 50 g of water. This solution was injected at a speed of 0.3 g/min into 185 g of the dimethyldichlorosilane placed in the flask. The reaction temperature was kept within the range of 0° to 5° C. by the external control.

Synthesis reactions were carried out under the same condition as described above, except that the content of water in the water solution introduced was changed variously. More specifically, the ratios of the water to the dimethyldichlorosilane in these reactions were 0.257, 0.500, 0.820 and 1.000, respectively, by mole. A small volume of the reaction product in each reaction was collected, and analyzed by gas chromatography. The thus determined yields of the reaction products and the water/dimethyldichlorosilane ratios (by mole) corresponding thereto are summarized in Table 6.

TABLE 6

| H$_2$O/(CH$_2$)$_2$SiCl$_2$ Ratio (by mole) | Yield (%) of Reaction Product | | | | | | | Note |
|---|---|---|---|---|---|---|---|---|
| | Linear Siloxane | | | Cyclic Siloxane | | | | |
| | 2,2-Dimer | 2,2-Trimer | 2,2-Tetramer | D$_3$ | D$_4$ | D$_5$ | D$_6$ | |
| 0.257 | 74 | 21 | 5 | 0 | 0 | 0 | 0 | Invention |
| 0.500 | 50 | 30 | 20 | 0 | 0 | 0 | 0 | Invention |
| 0.820 | 11 | 20 | 39 | 0 | 15 | 14 | 1 | Comparison |
| 1.000 | 0 | 0 | 0 | 0 | 68 | 27 | 5 | Invention |

It can be concluded that all the experimental results set forth above prove the validity of the present method.

What is claimed is:

1. A method of selectively producing cyclic dimethylpolysiloxanes, which comprises hydrolyzing dimethyldichlorosilane by contacting it with a water solution which contains a water-soluble oxygen-containing organic compound, and which has a water content of from 1.0 to 1.2 moles per mole of dimethyldichlorosilane, thereby selectively producing cyclic dimethylpolysiloxanes alone which are represented by the following general formula (II):

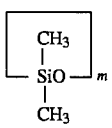

$$\left[ \begin{array}{c} CH_3 \\ | \\ SiO \\ | \\ CH_3 \end{array} \right]_m \quad (II)$$

wherein m is an integer of at least 3.

2. A method of producing cyclic dimethylpolysiloxanes according to claim 1, wherein the oxygen-containing organic compound is a compound selected from the group consisting of alcohols, ketones and cyclic ethers.

3. A method of producing cyclic dimethylpolysiloxanes according to claim 2, wherein the compound selected as the oxygen-containing organic compound is a dioxane, tetrahydrofuran or acetone.

4. The method of producing cyclic dimethylpolysiloxanes of claim 1, wherein the water-soluble oxygen-containing organic compound is methanol, ethanol, acetone, methyl ethyl ketone, 1,3-dioxane, 1,4-dioxane or tetrahydrofuran.

5. The method of producing cyclic dimethylpolysiloxanes of claim 1, wherein the water solution further contains an acid.

6. The method of producing cyclic dimethylpolysiloxanes of claim 5, wherein the acid is hydrochloric acid, sulfuric acid or acetic acid.

7. A method of producing cyclic dimethylpolysiloxanes according to claim 5, wherein the water solution has an acid/water ratio ranging from 0.001 to 0.35 by weight.

8. A method of producing cyclic dimethylpolysiloxanes according to claim 1, wherein the ratio of the weight of the water-soluble oxygen-containing organic compound to the weight of water in the water solution is from 0.1 to 10.

9. A method of producing cyclic dimethylpolysiloxanes according to claim 1, wherein the water solution is introduced into the dimethyldichlorosilane at a rate of 0.1 to 0.8 g/min per 100 g of dimethyldichlorosilane.

10. A method of producing cyclic dimethylpolysiloxanes according to claim 1, wherein the hydrolysis is carried out at a temperature of from 1° C. to 101° C.

11. The method of producing cyclic dimethylpolysiloxanes of claim 1, wherein in formula (II) m is from 3–14.

12. The method of producing cyclic dimethylpolysiloxanes of claim 1, wherein in formula (II) m is from 4–6.

13. The method of producing cyclic dimethylpolysiloxanes of claim 1, wherein the hydrolysis is conducted at a temperature of from 3°–30° C.

14. The method of producing cyclic dimethylpolysiloxanes of claim 1, wherein the yield of cyclic siloxanes is 100% and the yield of linear siloxanes is 0%.

15. The method of producing cyclic dimethylpolysiloxanes of claim 1, wherein the water-soluble oxygen-containing organic compound is an effective solvent for the hydrolysis reaction mixture.

* * * * *